(12) United States Patent
Shinbata

(10) Patent No.: US 6,901,158 B2
(45) Date of Patent: *May 31, 2005

(54) IMAGE DISCRIMINATION APPARATUS AND IMAGE DISCRIMINATION METHOD

(75) Inventor: Hiroyuki Shinbata, Utsunomiya (JP)

(73) Assignee: Canon Kabushiki Kaisha, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/154,805

(22) Filed: Sep. 17, 1998

(65) Prior Publication Data

US 2002/0114504 A1 Aug. 22, 2002

(30) Foreign Application Priority Data

Sep. 22, 1997 (JP) .............................................. 9-256894
Aug. 25, 1998 (JP) .......................................... 10-239101
Aug. 25, 1998 (JP) .......................................... 10-239103

(51) Int. Cl.$^7$ ................................................. G06K 9/00
(52) U.S. Cl. ...................... 382/132; 382/128; 378/98.4; 378/98.9
(58) Field of Search ............................... 382/132, 199, 382/128, 129, 130, 131; 378/98.3, 98.4, 108; 600/407

(56) References Cited

U.S. PATENT DOCUMENTS

| | | | | |
|---|---|---|---|---|
| 4,550,419 A | * | 10/1985 | Aichinger et al. | 378/98.4 |
| 5,091,970 A | | 2/1992 | Takeo | 382/48 |
| 5,289,374 A | * | 2/1994 | Doi et al. | 600/407 |
| 5,343,390 A | * | 8/1994 | Doi et al. | 364/413.16 |
| 5,369,572 A | * | 11/1994 | Haraki et al. | 364/413.13 |
| 5,426,684 A | * | 6/1995 | Gaborski et al. | 378/62 |
| 5,557,687 A | * | 9/1996 | Hara | 382/132 |
| 5,638,458 A | * | 6/1997 | Giger et al. | 382/132 |
| 6,031,892 A | * | 2/2000 | Karellas | 378/98.3 |

* cited by examiner

*Primary Examiner*—Bhavesh M. Mehta
*Assistant Examiner*—Abolfazl Tabatabai
(74) *Attorney, Agent, or Firm*—Morgan & Finnegan, L.L.P.

(57) ABSTRACT

An apparatus and method are provided for determining whether diaphragmatic radiation has been employed to obtain an autoradiograph of an object using a radiographic device having a diaphragmatic radiation function. An autoradiographic signal is entered and a first characteristic value is calculated using an autoradiograph designated by the autoradiographic signal, and then a frequency is calculated for the appearance of a density value for pixels constituting the edge of the autoradiograph that is determined using the first characteristic value and the frequency is employed to determine whether diaphragmatic radiation was used. So that preferable image processing can be performed, it is determined whether diaphragmatic radiation was employed in obtaining the autoradiograph, whether a designated portion in the autoradiograph is an irradiation area, and whether a plain image (an image produced when radioactive rays do not pass through an object but directly irradiate a sensor) is present/absent in the autoradiograph.

16 Claims, 16 Drawing Sheets

IMAGE DISCRIMINATION APPARATUS AND IMAGE DISCRIMINATION METHOD

BACKGROUND OF THE INVENTION

1. Field of the Invention

The present invention relates to an image discrimination apparatus and an image discrimination method for determining whether diaphragmatic radiation has been performed when an autoradiograph is obtained by irradiating a subject with radioactive rays using a radiographic device with a radiation diaphragm function, whether a designated area in the autoradiograph is an irradiated area, and whether a plain image (an area wherein a radioactive ray does not pass through a subject but is directly projected onto a sensor, etc.) is present in the autoradiograph. In particular, the present invention pertains to an image discrimination apparatus and an image discrimination method for identifying an autoradiograph by using the occurrence frequency at the edge portion, of a density value which is determined by a characteristic value obtained for the complete autoradiograph.

2. Related Background Art

Currently, in consonance, for example, with current digital techniques, autoradiographs are digitized, predetermined image processing is performed for the obtained digital images, and the resultant images are displayed on CRTs or are printed.

In radiography, "diaphragmatic radiation," the irradiation of only a required area 803 of a radiographic area 800 of a subject 801, i.e., as is shown in FIG. 1, is generally employed for humanitarian reasons and in order to eliminate scattering in an area 802 that is not required, and to prevent color contrast deterioration. Further, to perform predetermined image processing for a thus obtained autoradiograph, a process parameter is generally selected from among a distribution of density values in the irradiated image portion, and the image processing is performed in consonance with the selected processing parameters.

However, when a portion to be irradiated is not specified, a portion that is not needed may also be irradiated. Then, information concerning the unneeded portion, i.e., unneeded image information, must be employed to determine the processing parameters, and appropriate image processing can not be performed.

Therefore, the irradiated image portion is extracted from the autoradiograph, and only image information for a required portion of the irradiated image is thereafter employed to determine the processing parameters.

To extract an irradiated image portion, with one example method an image density value is used to perform a differential function, and the obtained differential value is employed to identify the edge portions (irradiation edges) of the irradiated area. According to another method, a linear approximation expression is used to obtain an approximate value for edge portions of an area other than the irradiated area, and the irradiation edge is identified by using the difference between the approximate value that is obtained and the actual density value.

These methods are based on the assumption that an image was obtained by performing a diaphragmatic radiation process. Therefore, as the pre-processing performed for these methods, a determination is made as to whether the autoradiograph was obtained by using diaphragmatic radiation (the image was subjected to diaphragmatic radiation, as is shown in FIG. 1) or without using diaphragmatic radiation (the image was not subjected to diaphragmatic radiation, as is shown in FIG. 2).

To determine whether diaphragmatic radiation was employed, one method calls for the average density value or the middle density value in the center of the image to be compared with the average density value at the edge of the image, and when the average density value at the edge of the image is equal to or smaller than a predetermined value, it is ascertained that the image was obtained by using diaphragmatic radiation.

With the above described conventional image discrimination methods, however, when an arbitrary subject is radiographed without diaphragmatic radiation being used and the radiographic area includes the edge portion of the subject, the average density value at the edge of the obtained image varies in consonance with the size of the image portion, which includes the edge of the subject, and with the transmittance of radioactive rays. Therefore, even when the image is obtained without using diaphragmatic radiation, it may erroneously be determined that diaphragmatic radiation was used.

FIG. 3 shows an image obtained by autoradiography of the front of the lungs, using an X-ray. The reference a denotes an entire image, and the reference b denotes an irradiated area which is directly irradiated by the X-ray. A black portion included in the area b is a portion where the X-ray is directly incident onto a sensor. The reference A denotes an area to be used to discriminate whether the diaphragmatic radiation is employed or not.

With a method for discriminating whether or not the diaphragmatic radiation is employed, according to whether the portion A is irradiated by the X-ray or not, it can not be discriminated to which extent the diaphragm is opened, while such the method can discriminate whether or not the diaphragm is employed. Thus, since rough information as to the irradiated area is not obtained, a processing for extracting the irradiated area should be performed over the entire area. This may result in a problem that many time is required to perform such the process. In addition, even if the irradiated area is extracted, inspection of the extracted irradiated area can not be performed since the outline of the irradiated area is unknown.

Further, as is shown in FIG. 3, when the area on the sensor that is directly irradiated by X-rays is small, for lungs, the change in the density will be greater at the periphery of the lungs than at the irradiation edge, and the periphery of the lungs will be erroneously extracted as the irradiated area.

In addition, when the irradiated area includes the edge of the image and diaphragmatic radiation was not employed, the average density at the edge of the image fluctuates in consonance with the size of the irradiated area, which includes the edge of the image, and with the transmittance of radioactive rays. Therefore, a problem that has arisen is that it may be erroneously ascertained that diaphragmatic radiation has been employed, even though it has not. Another problem that has arisen is that when the intensity of radioactive rays is low there is no difference in the densities at the center of the image and at its edge, so that it will be erroneously ascertained that diaphragmatic radiation has been performed, even though it has not.

Furthermore, as image processing for an autoradiograph, there is a gradation conversion process for performing gradation conversion in accordance with the density distribution for an original image that is radiographed. For example, as data for a feature, the maximum density value is extracted from the original image, and the density value for the original image is so changed that the maximum density value is set to a predetermined value.

Generally, "diaphragmatic radiation" for radiating only a required portion of a subject is employed for radiography. This is done for humanitarian reasons, and in order to eliminate scattering in an unneeded area and to prevent color contrast deterioration.

In FIG. 4 is shown an X-ray image of lungs that were radiographed from the front and for which diaphragmatic radiation was not employed, and in FIG. 5 is an X-ray image of lungs that were radiographed from the front and for which diaphragmatic radiation was employed.

In FIGS. 4 and 5, an area 601 is an irradiation area (sensor portion), and a shaded portion 602 in FIG. 4 is a portion (plain image) obtained by directly irradiating the sensor with X-rays. An area 603 in FIG. 5 is a portion that is directly irradiated with X-rays when diaphragmatic radiation is employed. A plain image is not present in the portion 603, but tends to appear when diaphragmatic radiation is not employed for a subject.

In order to perform the gradation conversion process for the X-ray images (original images) shown in FIGS. 4 and 5, first, a check is performed to determine whether a plain image is present in the original image to be processed. When a plain image is present, it is removed from the original image. Then, for example, the maximum density value in the remaining portion is extracted as the maximum density value for the lung area, and the density value for the original image is so changed that the maximum density value for the film is approximately 2.0.

However, for the above described gradation conversion process, even though no plain image is present in an X-ray image obtained when diaphragmatic radiation is employed (see FIG. 5), conventionally it may erroneously be ascertained that the lung portion in the X-ray image is a plain image. Therefore, data for the feature of an image (e.g., the maximum density value in the lung portion), which are required for the gradation conversion process, can not be obtained.

SUMMARY OF THE INVENTION

It is one objective of the present invention to provide an image discrimination apparatus and an image discrimination method for resolving the above described shortcomings.

It is another objective of the present invention to provide an image discrimination apparatus and an image discrimination method for precisely determining whether diaphragmatic radiation was performed when an autoradiograph of a subject was obtained using a radiographic device with a diaphragmatic radiation function.

To achieve this objective, according to one aspect of the present invention, an image discrimination apparatus, which determines whether diaphragmatic radiation has been performed to obtain an autoradiograph of a subject using a radiographic device with a diaphragmatic radiation function, comprises:

first characteristic value calculation means for entering an autoradiographic signal and for calculating a first characteristic value by using an autoradiograph designated by the autoradiographic signal;

occurrence frequency calculation means for calculating a frequency for a density value of a pixel that constitutes the edge of the autoradiograph that has been determined by using the first characteristic value obtained by the first characteristic value calculation means; and first discrimination means for employing the frequency obtained by the occurrence frequency calculation means to determine whether the autoradiograph has been obtained by using diaphragmatic radiation.

It is an additional objective of the present invention to provide an image discrimination apparatus and an image discrimination method for precisely determining whether a designated portion in an autoradiograph of a subject, which has been obtained by a radiographic device having a diaphragmatic radiation function, is an irradiation area.

To achieve this additional objective, according to another aspect of the present invention, an image discrimination apparatus, which determines whether a designated portion of an autoradiograph of a subject is an irradiation area, comprises:

first characteristic value calculation means for entering an autoradiographic signal and for calculating a first characteristic value by using an complete autoradiograph indicated by the autoradiographic signal;

second characteristic value calculation means for calculating second characteristic values, one for each of a plurality of designated portions of the autoradiograph; and discrimination means for comparing the first characteristic value, obtained by the first characteristic value calculation means, with each of the second characteristic values, obtained by the second characteristic value calculation means, to determine whether each of the plurality of designated portions of the autoradiograph is an irradiation area.

It is a further objective of the present invention to provide an image discrimination apparatus and an image discrimination method for precisely determining the presence/absence of a plain image (an image obtained when radioactive rays do not pass through a subject, and instead, directly irradiate a sensor) in the autoradiograph of a subject that is obtained by a radiographic device having a diaphragmatic radiation function, and for performing preferable image processing.

To achieve this further objective, according to an additional aspect of the present invention, an image discrimination apparatus, which detects the presence/absence of a plain image in an autoradiograph of a subject that is obtained by a radiographic device having a diaphragmatic radiation function, comprises:

characteristic value getting means for entering an autoradiograph signal and for getting a characteristic value from an autoradiograph designated by the autoradiographic signal;

frequency acquisition means for obtaining an occurence frequency of the pixels that constitute the edge of an irradiation area in the autoradiograph, that has a density value that is determined using the characteristic value obtained by the characteristic value getting means; and discrimination means for employing the occurrence frequency obtained by the frequency acquisition means to detect the presence/absence of a plain image in the autoradiograph.

The other objectives and features of the present invention will become apparent during the course of the detailed description of the preferred embodiments given while referring to the following drawings.

DETAILED DESCRIPTION OF THE PREFERRED EMBODIMENTS

The preferred embodiments of the present invention will now be described.

First, a first embodiment will be explained.

Figure 6:
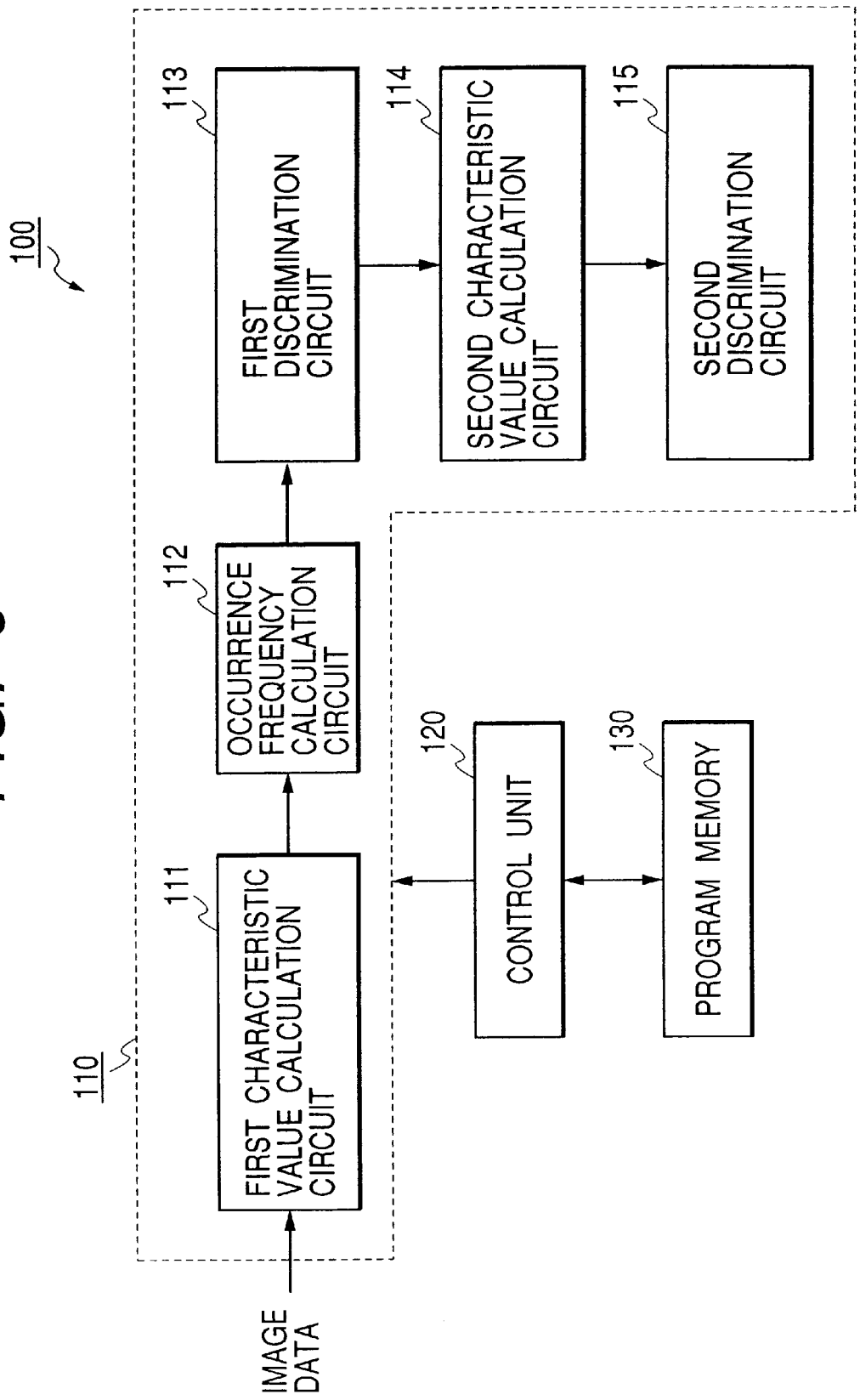
FIG. 6 is a block diagram illustrating the arrangement of an image discrimination apparatus according to a first embodiment of the present invention.

An image discrimination method according to the present invention is performed, for example, by an image discrimination apparatus 100 shown in FIG. 6. An image discrimination apparatus according to the present invention is applied for this image discrimination apparatus 100.

Specifically, as is shown in FIG. 6, the image discrimination apparatus 100 comprises a discrimination unit 110; a control unit 120 for controlling the operation of the discrimination unit 110; and a program memory 130 that is accessed by the control unit 120.

Figure 7:
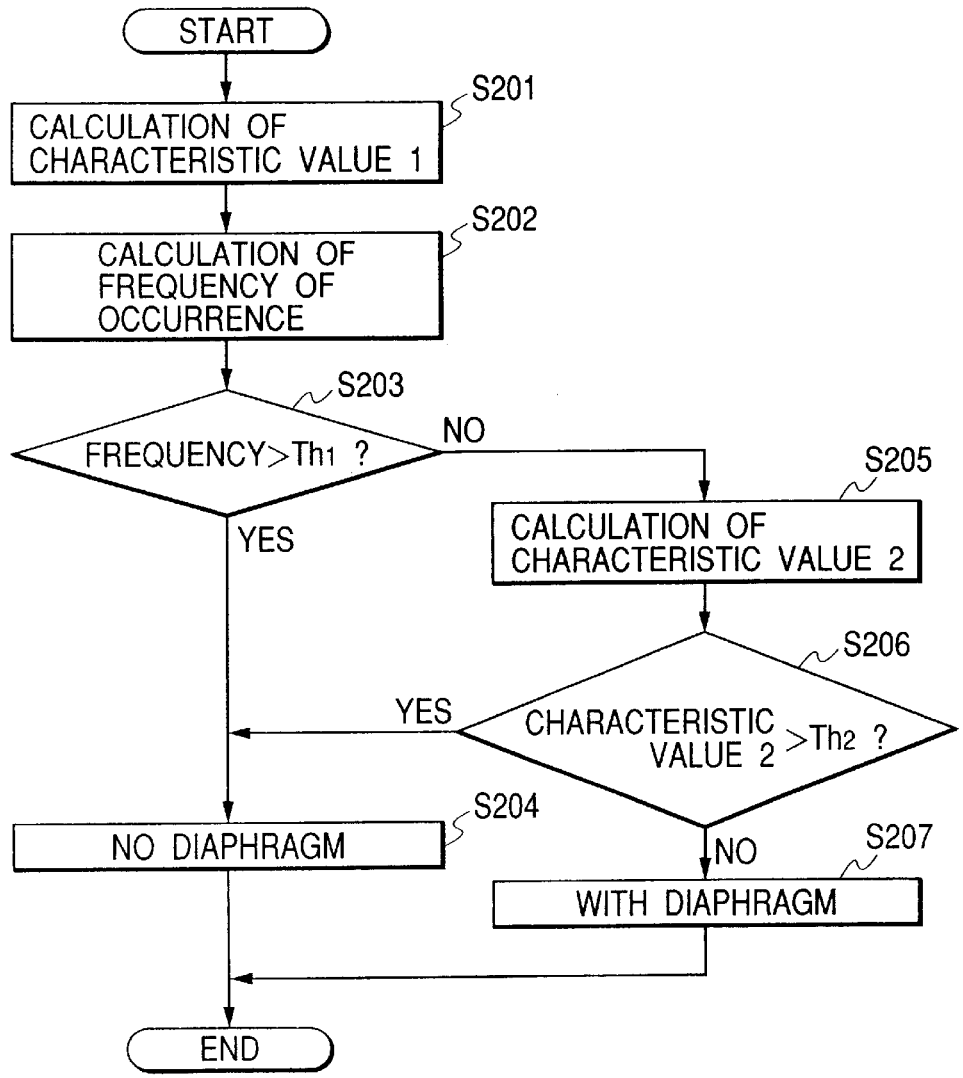
FIG. 7 is a flowchart for explaining a processing program executed by the image discrimination apparatus.

A processing program, described in the flowchart shown in FIG. 7, is stored in advance in the program memory 130, for example. When this processing program is read and executed by the control unit 120, the operation of the discrimination unit 110, which will be described later, is performed.

A memory medium according to the present invention is applied for the program memory 130 in which the processing program in FIG. 7 is stored.

The discrimination unit 110 includes: a first characteristic value calculation circuit 111, for calculating a first characteristic value by using image data that are input; an occurrence frequency calculation circuit 112, for calculating a frequency at which a density value that is determined based on the first characteristic value obtained by the first characteristic value calculation circuit 111 appears at the edge of an image; a first discrimination circuit 113, for employing the frequency obtained by the occurrence frequency calculation circuit 112 to determine whether the input image data are those obtained by using diaphragmatic radiation or those obtained without using diaphragmatic radiation; a second characteristic value calculation circuit 114, for calculating a second characteristic value at the edge of the image in consonance with the result obtained by the first discrimination circuit 113; and a second discrimination circuit 115, for employing the second characteristic value obtained by the second characteristic value calculation circuit 114 to determine whether the input image data are those obtained by using diaphragmatic radiation or those obtained without using diaphragmatic radiation.

When the processing program in FIG. 7, which is stored in the program memory 130, is read and executed by the control unit 120, the thus arranged discrimination unit 110 is operated as follows.

Figure 8:
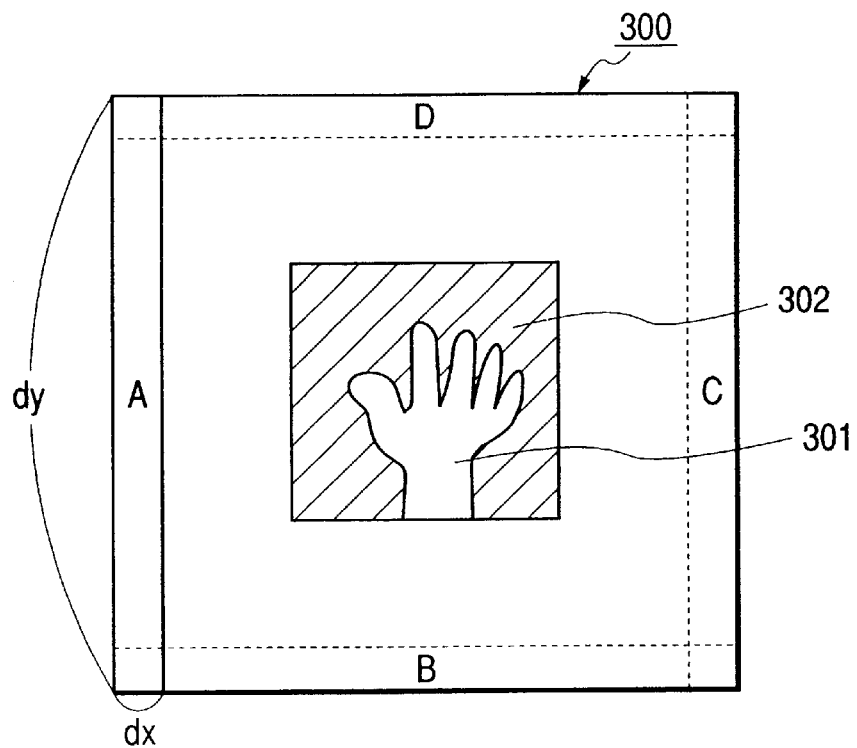
FIG. 8 is a diagram for explaining the calculation, performed by an occurrence frequency calculation circuit in the image discrimination apparatus, of a frequency at which a density value appears at the edge of an image.

Assume that data for an autoradiographic image 300 shown in FIG. 8 are input to the discrimination unit 110. In FIG. 8 an area 301 is an object and an area 302 is an irradiation area.

First, the first characteristic value calculation circuit 111 calculates as a first characteristic value S1 a value MAX for the entire image 300 (step S201).

Assume that the value MAX in this case is, for example, the upper point (e.g., 5% point) in the cumulative histogram for the complete image 300.

It should be noted that the value MAX is not limited to the upper point in the cumulative histogram of the image 300, but that the density values for the entire image 300 may be sorted and the upper point may be employed as the value MAX.

The occurrence frequency calculation circuit 112 calculates a frequency at which a density value that has a constant ratio, e.g., 90%, of the first characteristic value $S_1$, which is obtained by the first characteristic value calculation circuit 111, has appeared at the edge portion A (left edge) of the image in FIG. 8 (step S202).

It should be noted that the edge portion A of the image is an area having a horizonal width dx and a vertical width dy.

Following this, the first discrimination circuit 113 determines whether the frequency obtained by the occurrence frequency calculation circuit 112 is greater than a constant value $Th_1$ (step S203).

When the occurrence frequency $>Th_1$, the first discrimination circuit 113 ascertains that the input image data are those for an image obtained without using diaphragmatic radiation (step S204). The processing is thereafter terminated.

When the occurrence frequency $>Th_1$ is not established, the first discrimination circuit 113 ascertains that the input image data are those for an image obtained by using diaphragmatic radiation. Program control then moves to step S205.

Specifically, when the occurrence frequency $>Th_1$ is not established, the second characteristic value calculation circuit 114 calculates a standard deviation value $S_2$ for density value $f(x, y)$ of the image edge portion A, as is shown in equation (1), $$S_2 = \sqrt{\int_0^{dy}\int_0^{dx}(f(x, y) - \overline{f}(x, y))^2 dx dy} \quad (1)$$

$$\overline{f}(x, y) = \frac{\int_0^{dy}\int_0^{dx} f(x, y)dx dy}{\int_0^{dy}\int_0^{dx} dx dy},$$

and the standard deviation value $S_2$ is used as the second characteristic value $S_2$ (step S205).

The second discrimination circuit 115 determines whether the second characteristic value $S_2$ obtained by the second characteristic value calculation circuit 114 is a constant value $Th_2$ (step S206).

When the second characteristic value $S_2 > Th_2$, the second discrimination circuit 115 ascertains that the input image data are those for an image obtained without using diaphragmatic radiation (step S204). The processing is thereafter terminated.

When the second characteristic value $S_2 > Th_2$ is not established, the second discrimination circuit 115 ascertains that the input image data are those for an image obtained by using diaphragmatic radiation (step S207). The processing is thereafter terminated.

The above described steps are also performed for lower edge B, right edge C, and upper edge D of the image 300.

As is described above, in the first embodiment, the frequency at which the density value is determined for the complete image 300 using the value MAX is employed to determine whether the autoradiograph is obtained by using diaphragmatic radiation or by not using it. Therefore, even for an image wherein the object 301 includes the edge of the irradiation area 302, a consistent determination process can be performed.

In addition, when at step S203 the image is one that is obtained by using diaphragmatic radiation, the standard deviation is calculated as the second characteristic value $S_2$ by using the edge portions (A to D) of the image, and is employed to determine whether the image has been obtained by using diaphragmatic radiation or by not using it. As a result, even when the object 301 includes all the edge portions (A to D) of the image, a consistent determination process can be performed.

In the first embodiment, as is shown in equation (1), the standard deviation value for the density value $f(x, y)$ at the edge of the image is obtained as the second characteristic value $S_2$. However, the second characteristic value $S_2$ is not limited to this definition. For example, as is shown in equation (2), $$S_2 = \frac{\sqrt{\int_0^{dy}\int_0^{dx}(f(x, y) - \overline{f}(x, y))^2 dx dy}}{\overline{f}(x, y)}, \quad (2)$$

the standard deviation value for the density value $f(x, y)$ at the edge of the image may be normalized using the average of the density value $f(x, y)$, and the resultant value may be employed as the second characteristic value $S_2$.

As a result, regardless of the intensity of the radioactive rays, i.e., when the intensity of radioactive rays is low, or when the object 301 includes all edge portions (A to D) of the image, a consistent determination can be provided.

A second embodiment will now be described.

In the second embodiment, the first characteristic value calculation circuit 111 in FIG. 6 calculates a first characteristic value $S_1$ by using a density value histogram.

Figure 9:
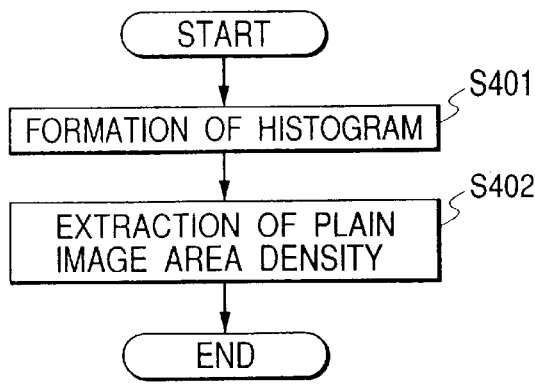
FIG. 9 is a flowchart for explaining a processing program to be executed by a first characteristic value calculation circuit in an image discrimination apparatus according to a second embodiment of the present invention.

Specifically, when the processing program shown in the flowchart in FIG. 9 is read and executed, the first characteristic value calculation circuit 111 is operated as follows.

It should be noted that the processing program in FIG. 9 is stored in advance in a program memory 130, and is read and executed by a control unit 120.

Furthermore, a memory medium according to the present invention is employed for the program memory 130 in which the processing program is stored.

Figure 10:
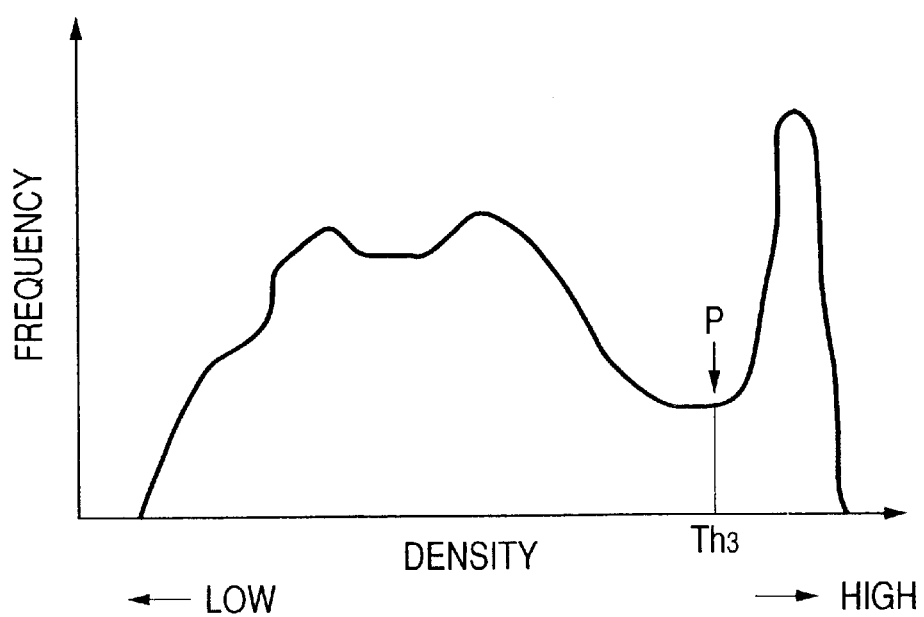
FIG. 10 is a graph for explaining a density value histogram that is formed by the first characteristic value calculation circuit of the image discrimination apparatus of the present invention.

First, the first characteristic value calculation circuit 111 forms the histogram shown in FIG. 10 (step S401).

Then, the first characteristic value calculation circuit 111 extracts from the histogram a density value $Th_3$ that indicates the lower density limit in a plain image (step S402).

In this embodiment, the density value $Th_3$ is the deepest point P in a first dent portion of the maximum density value shown in the histogram.

The first characteristic value calculation circuit 111 defines as the first characteristic value $S_1$ the extracted density value $Th_3$.

Therefore, an occurrence frequency calculation circuit 112 at the following stage calculates the frequency at which a density value that is equal to or higher than a constant ratio of the thus obtained first characteristic value $S_1$ (the density value $Th_3$) appears at the edge of the image.

As is described above, in the second embodiment, when a plain image is present, the density value in that portion can be calculated consistently. Therefore, whether an image has been obtained by using diaphragmatic radiation or without using such radiation can be accurately determined.

The objectives of the present invention are achieved as follows: a memory medium on which is stored software program code for implementing the functions of a host computer or a terminal in the first and the second embodiments is supplied to a system or to an apparatus, and the computer (or a CPU or an MPU) in the system or the apparatus reads the program code from the memory medium.

In this case, the program code read from the memory medium accomplishes the functions of the above described embodiments, and the memory medium on which such program code is recorded constitutes the present invention.

A memory medium for supplying such program code can be, for example, a ROM, a floppy disk, a hard disk, an optical disk, a magneto optical disk, a CD-ROM, a CD-R, a magnetic tape or a nonvolatile memory card.

In addition, the scope of the present invention includes not only a case where the functions in the first and the second embodiments can be performed when program code is read and executed by the computer, but also a case where, according to an instruction in the program code, an OS running on the computer, etc., performs one part, or all, of the actual processing to accomplish the functions included in the above embodiments.

Furthermore, in order to implement the functions included in the first and the second embodiments, the present invention includes a case where program code, read from a memory medium, is written in a memory that is mounted on a function expansion board inserted into a computer, or a function expansion unit connected to a computer, and in consonance with a program code instruction, a CPU mounted on the function expansion board, or on the function expansion unit, performs one part, or all, of the actual processing.

A third embodiment will now be explained.

Figure 12:
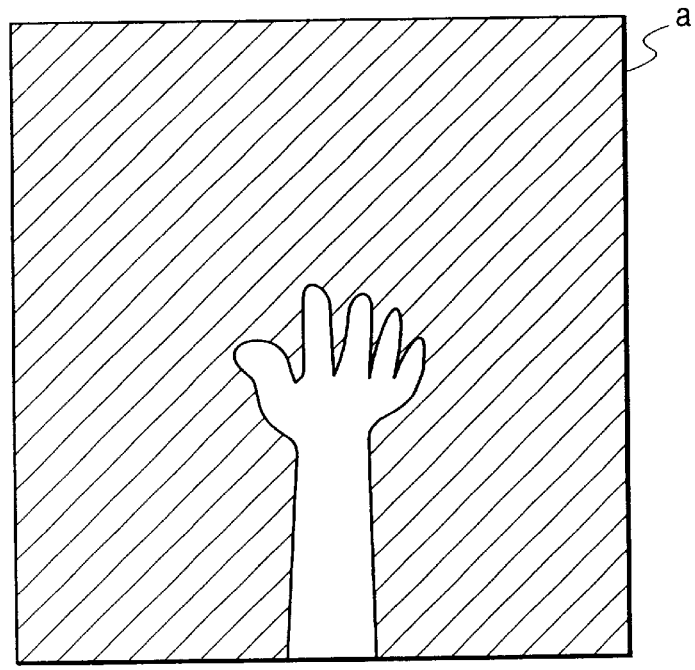
FIG. 12 is a diagram showing an autoradiograph of the hand of a patient obtained without using diaphragmatic radiation.

In FIG. 12 is shown the autoradiograph of a hand provided without using diaphragmatic radiation. An area a denotes the complete image.

Figure 13:
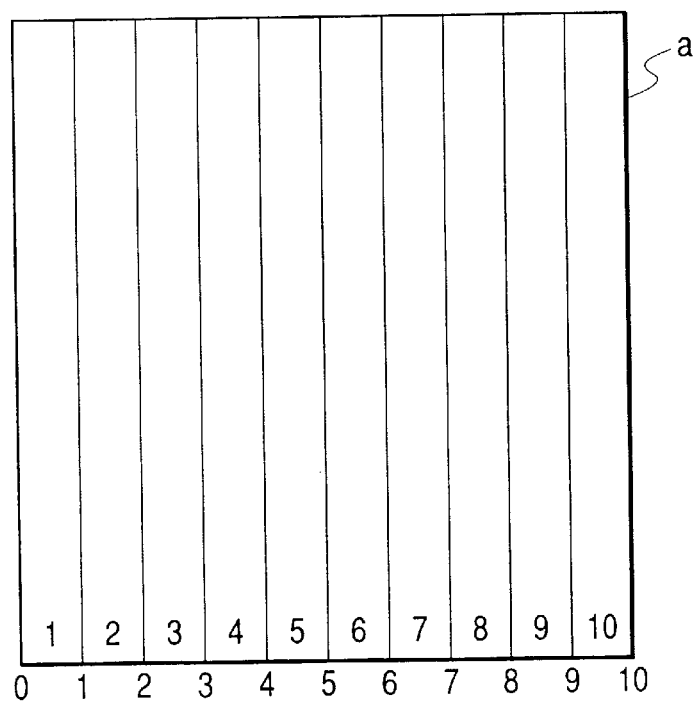
FIG. 13 is a diagram showing example designated portions.

In FIG. 13 are shown ten designated areas, 1 to 10, that are obtained by dividing the complete image area a. The numerals in at the lower portion designate coordinates.

Figure 14:
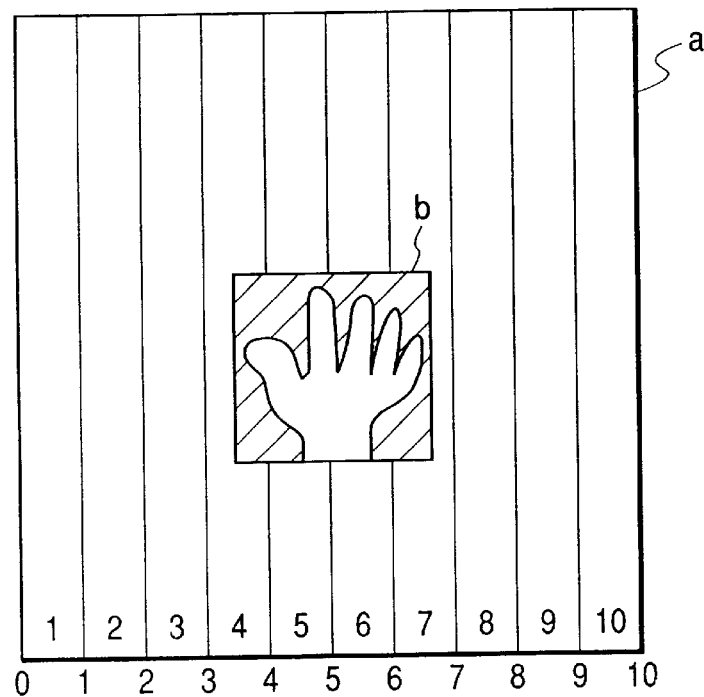
FIG. 14 is a diagram showing both an autoradiograph of the hand of a patient that is obtained by using diaphragmatic radiation and designated portions of the autoradiograph.

In FIG. 14 are shown the autoradiograph (portion b) of a hand obtained by using diaphragmatic radiation, and how it is related to the designated areas in FIG. 13.

Figure 15:
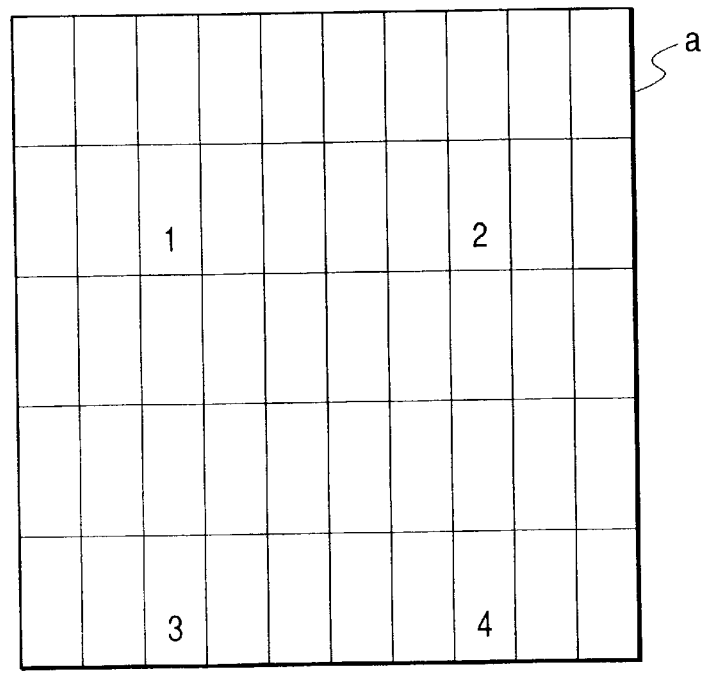
FIG. 15 is a diagram showing another example of designated portions.

In FIG. 15 are shown 50 designated areas obtained by dividing the complete image portion a.

Figure 16:
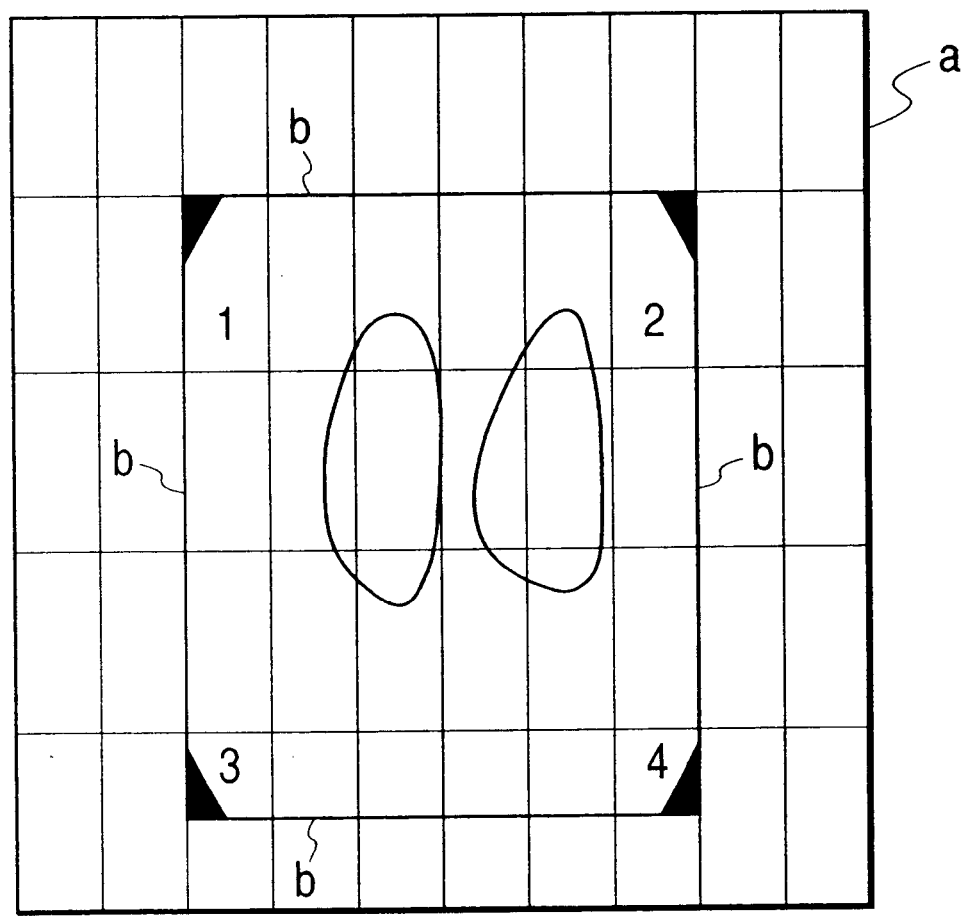
FIG. 16 is a diagram showing both an autoradiograph of the chest of a patient that is obtained by using diaphragmatic radiation, and designated portions of the autoradiograph.

In FIG. 16 are shown an autoradiograph of lungs (portion b) obtained by using diaphragmatic radiation and how it is related to the designated areas in FIG. 15.

Figure 11:
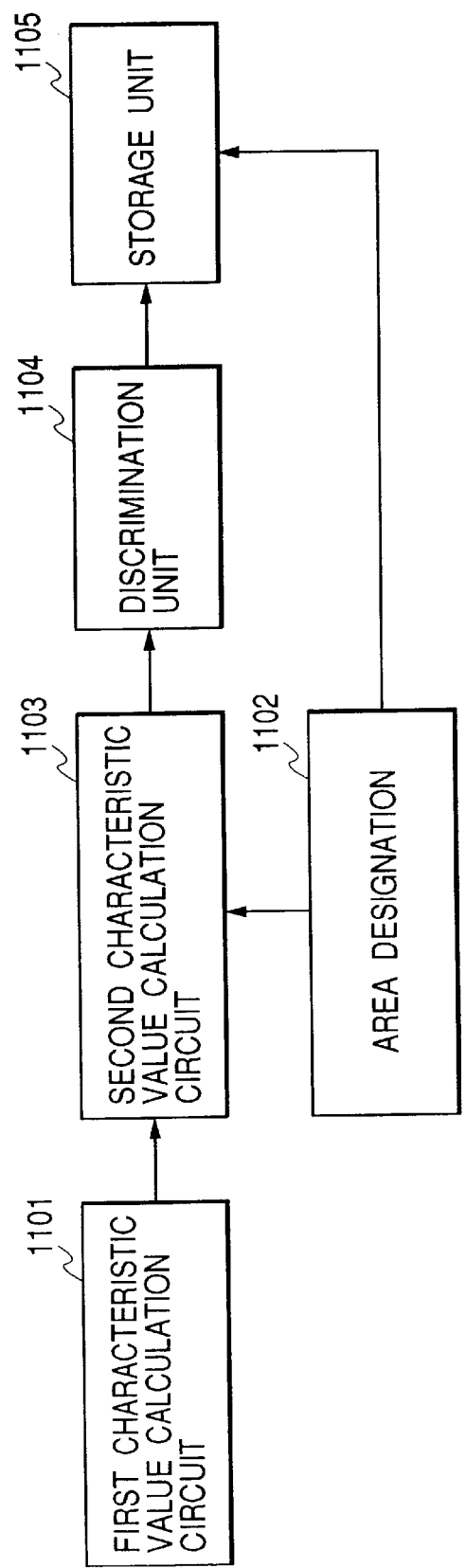
FIG. 11 is a block diagram illustrating the arrangement of an image discrimination apparatus according to a third embodiment of the present invention.

FIG. 11 is a block diagram illustrating the arrangement of an irradiated area discrimination apparatus according to the third embodiment of the present invention.

In FIG. 11, the irradiated area discrimination apparatus comprises: a first characteristic value calculation unit 1101, for calculating a first characteristic value for the entire image; an area designation unit 1102, for designating an area for which a second characteristic value is to be calculated; a second characteristic value calculation unit 1103, for calculating, as the second characteristic value, a density value in an area designated by said area designation unit 1102; a discrimination unit 1104, for employing the second characteristic value to determine whether an irradiated area is present in the designated area; and a storage unit 1105, for storing area information received from the area designation unit 1102 and the result obtained by the discrimination unit 1104.

Figure 17:
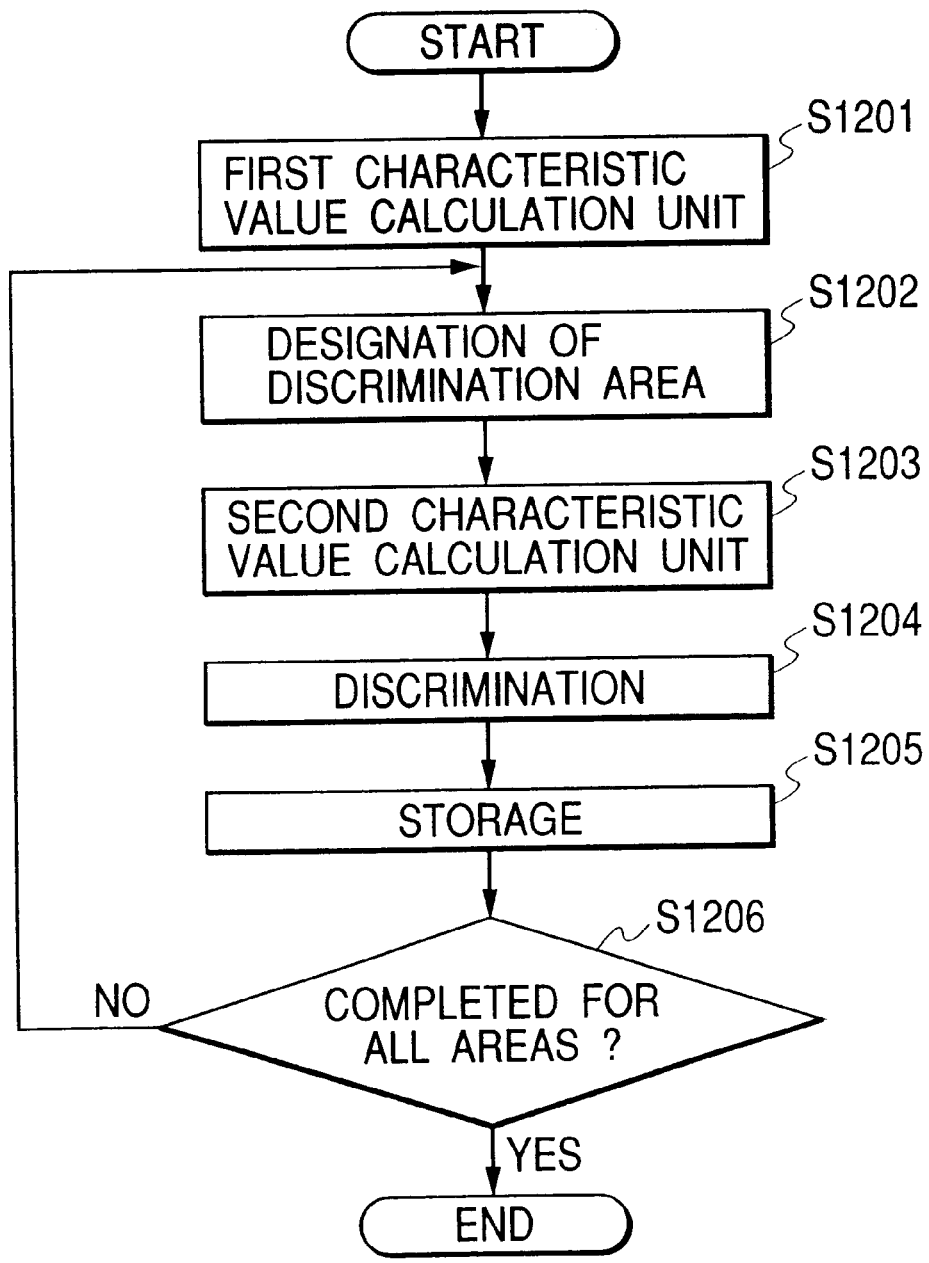
FIG. 17 is a flowchart showing the processing performed by an image discrimination apparatus according to a fourth embodiment of the present invention.

The processing performed by the irradiated area discrimination apparatus will now be explained while referring to the flowchart in FIG. 17. Here, the processing for determining whether the designated area is an irradiated area will be explained while referring to FIG. 14.

The first characteristic value calculation unit 1101 calculates the MAX density value for the entire image. The value MAX can be the upper point of the cumulative histogram for the complete image, i.e., a 5% point, or the image density values may be sorted and an upper point may be defined as the value MAX.

A density value d1 represented by equation (3) is regarded as the first characteristic value (step S1201), $$d1 = MAX \times ratio \qquad (3),$$

wherein "ratio" is a constant, e.g., 0.5.

The area designation unit 1102 sequentially designates the areas 1 to 10 shown in FIG. 13, and transmits coordinate information for the designated areas to the second characteristic value calculation unit 1103 (step S1202).

Upon receipt of this information, the second characteristic value calculation unit 1103 calculates the average density value for the designated areas and regards the average value as the second characteristic value d2 (step S1203). The discrimination unit 1104 then compares the first characteristic value d1 with the second characteristic value d2. When the result is $$d2 > d1 \qquad (4),$$

it is ascertained that the designated areas are irradiated areas, but for the other cases, it is ascertained that the designated areas are not irradiated areas (step S1204).

Following this, the storage unit 1105 stores the coordinates for the designated areas and the result obtained by the discrimination unit 1104 (step S1205). When second characteristic values have been acquired for all the designated areas, the processing is terminated. When second characteristic values for all the designated areas have not yet been acquired, program control returns to step S1202, and the process from step S1203 to S1205 is repeated for the remaining designated areas.

As is described above, a designated area that is an irradiated area can be extracted by comparing the first characteristic value and the second characteristic value for the designated area.

In the example in FIG. 14, the discrimination unit 1104 determines that the irradiation area includes designated areas 4, 5, 6 and 7. Thus, it is assumed that the left edge of the irradiation area is located between coordinates 3 and 4, and the right edge is located between coordinates 6 and 7. As a result, the processing for acquiring the left edge of the irradiation area need only be performed between the coordinates 3 to 7, and the time required for performing the calculation is shorter than the time required for processing all the coordinates.

In addition, when a specific irradiation area extraction method is used to extract an irradiation area, since the left irradiation edge is located within the designated area 4, it can be determined that areas other than the designated area 4 have been mistakenly extracted. And when it is determined that an extraction error has occurred, another irradiation area extraction method can be employed.

Since in the autoradiograph in FIG. 16, for example, only a small portion of a sensor is irradiated with X-rays, the peripheral edges of the lungs tend to be extracted mistakenly. In this embodiment, however, it can be determined that the irradiation area includes at least the designated areas 1, 2, 3 and 4 in FIG. 16. Therefore, when the edges of the lungs are mistakenly extracted as the irradiation edges, this extraction can be determined to have been an error, and the area information for the designated areas 1, 2, 3 and 4 can be employed to newly extract the irradiation area.

In this embodiment, the maximum density value for the complete image is employed as the first characteristic value, but the average density value or the middle density value for the image may also be employed. The average density value or the middle density value for the designated areas may also be employed as the second characteristic value.

As is described above, according to the third embodiment, since the irradiation area extraction process is performed by determining whether the irradiation area is present or absent in the designated area, the entire area, therefore, need not be processed, and the calculation time can be reduced.

Furthermore, the result obtained by the irradiation area extraction process can be verified by determining whether the irradiation area is present in the designated area. When the irradiation area is mistakenly extracted, the irradiation area extraction process can be performed again, and the accuracy in the extraction of the irradiation area can be enhanced.

Further, when an extraction error occurs, another irradiation area extraction method can be employed, and the accuracy in the extraction of an irradiation area can be improved by employing a combination of a plurality of irradiation area extraction methods.

A fourth embodiment will now be described.

In this embodiment, the characteristic value calculation method employed by a second characteristic value calculation unit 1103 in FIG. 11 and the discrimination method employed by a discrimination unit 1104 differ from those in the third embodiment. The processing in FIG. 17 for determining the presence/absence of the irradiation area will now be described by using the examples in FIGS. 12 and 14.

First, a first characteristic value calculation unit 1101 calculates the value MAX for the entire image. The value MAX may be the upper point in the cumulative histogram for the entire image, i.e., a 5% point, or the image density values may be sorted and the upper point may be employed as the value MAX (step S1201).

Then, an area designation unit 1102 sequentially designates designated areas 1 to 10 in FIG. 13, and transmits coordinate information for the designated areas to the second characteristic value calculation unit 1103 (step S1202).

The second characteristic value calculation means 1103 calculates the frequency of the appearance, in the designated area, of a density value having a constant ratio, e.g., 90%, of the value MAX that is obtained by the first characteristic value calculation unit 1101 (step S1203).

When the frequency obtained by the second characteristic value calculation means 1103 is greater than a predetermined value $Th_1$ (e.g., $Th_1=0.05$), a discrimination unit 1104 determines that the designated area is an irradiation area; and when the frequency is equal to or smaller than the value $Th_1$, the discrimination unit 1104 determines that the designated area is not an irradiation area (step S1204). The storage unit 1105 stores the coordinates of the designated area and the result obtained by the discrimination unit 1104 (step S1205). When a second characteristic value has been obtained for all the designated areas, the processing is terminated. If second characteristic values for all the designated areas have not yet been obtained, program control returns to step S1202, and the process at steps S1203 to S1205 is repeated for the remaining designated areas.

As is described above, according to the fourth embodiment, even when a metal piece is present in the designated area, since instead of the average density value the frequency is employed as the second characteristic value, a consistent determination can be provided that is not affected by the density value of the metal piece. Furthermore, since the frequency is employed, the determination is consistent and is not affected by noise at a high density or a low density.

A fifth embodiment will now be explained.

Figure 18:
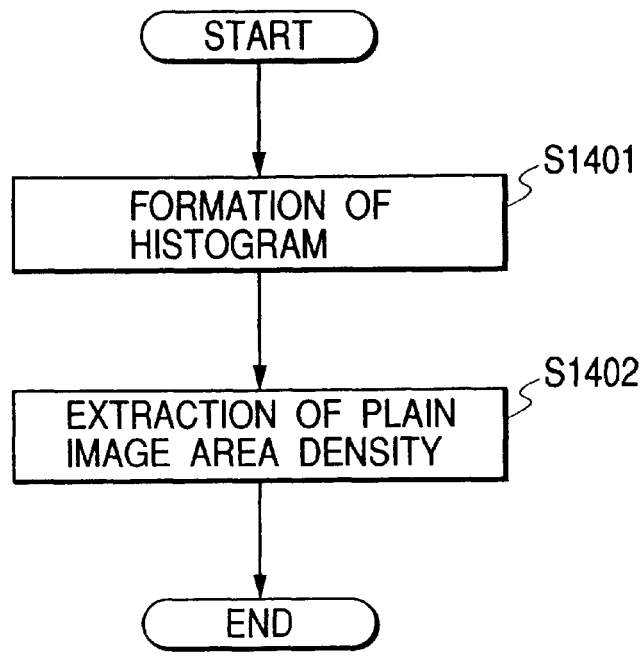
FIG. 18 is a flowchart showing the processing performed by an image discrimination apparatus according to a fifth embodiment of the present invention.
Figure 19:
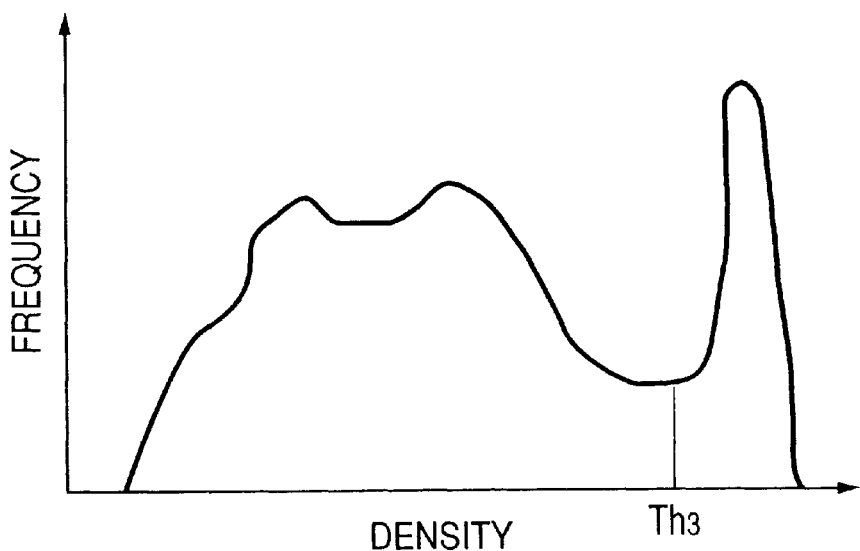
FIG. 19 is a characteristic graph showing a histogram for density values of a complete autoradiograph.

FIG. 18 is a flowchart showing the first characteristic value calculation processing performed by a first characteristic value calculation unit 101 according to the fifth embodiment. FIG. 19 is a graph for a density value histogram for the entire image, while the horizontal axis represents a density value, and the vertical axis represents an occurrence frequency.

The processing will now be described while referring to FIG. 18.

First, a histogram shown in FIG. 19 is formed (step S1401). Then, a density value $Th_3$, which indicates the lower density limit in a plain image (a portion wherein a sensor is directly irradiated with X-rays), is extracted from the histogram. The deepest point in the first dent portion on the high density side in the histogram in FIG. 19 is defined as the value $Th_3$ (step S1402). The value $Th_3$ is regarded as the value MAX calculated by the first characteristic value calculation unit 1101. The following process is performed in the same manner as is described in the fourth embodiment.

As is described above, according to the fifth embodiment, when a plain image is present, the density in that area can be constantly calculated. And this density value and the characteristic value obtained for the designated area can be employed to consistently extract the designated area, which is the plain image.

A memory medium according to the present invention will now be described.

When a system comprising the blocks in FIG. 11 is constituted by a computer system that includes a CPU and a memory such as a ROM, a memory medium according to the present invention is employed for the above memory. In this memory medium a program is stored for executing the processing described while referring to the flowchart in FIG. 17 or 19.

Such a memory medium can, for example, be a semiconductor memory such as a ROM or a RAM, an optical disk, a magneto optical disk, a magnetic medium, a CD-ROM, a floppy disk, a magnetic card, or a nonvolatile memory card.

Therefore, when this memory medium is employed for the system and the apparatus shown in the above drawings, or for another system or apparatus, and the system or the computer reads and executes program code stored in the memory medium, the same function and effects as in the above embodiments can be obtained and the objectives of the present invention can be achieved.

In addition, the same function and effects as in the above embodiments can be obtained, and the objectives of the present invention can be achieved not only in a case where an OS running on the computer performs one part, or all, of the actual processing, but also in a case where program code, read from a memory medium, is written in a memory that is mounted on a function expansion board inserted into a computer, or a function expansion unit connected to a computer, and in consonance with a program code instruction, a CPU mounted on the function expansion board, or on the function expansion unit, performs one part, or all, of the processing.

Figure 20:
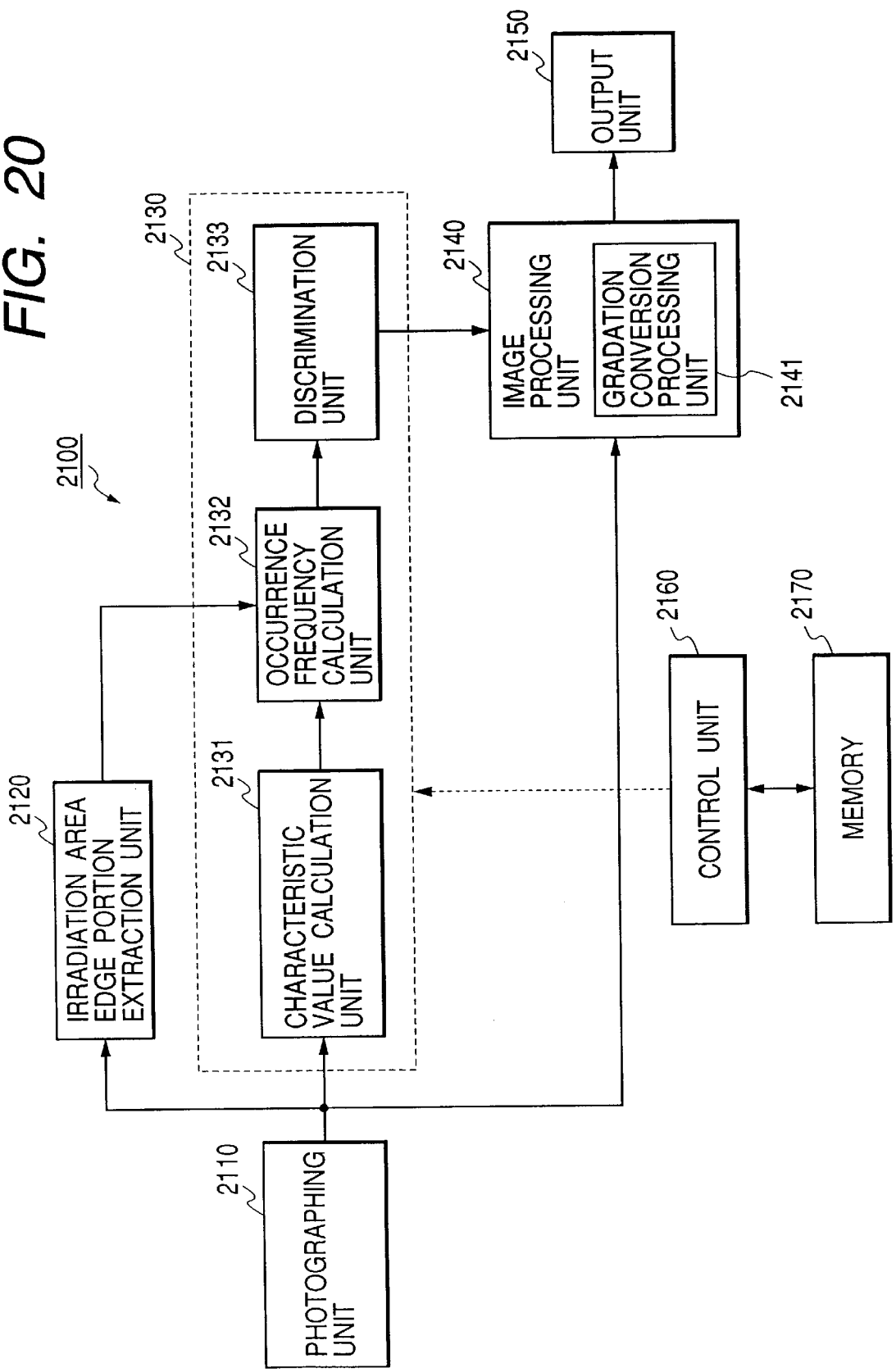
FIG. 20 is a block diagram illustrating the arrangement of an image discrimination apparatus according to a sixth embodiment of the present invention.

In a sixth embodiment, the present invention is applied for an image processing apparatus 2100 in FIG. 20.

The image processing apparatus 2100 comprises: a photography unit 2110, for irradiating the front of the lungs with X-rays to obtain an image; an irradiation area edge portion extraction unit 2120, for receiving the image data from the photography unit 2110; an image discrimination unit 2130, for receiving the data from the photography unit 2110 and the irradiation area edge portion extraction unit 2120; an image processing unit 2140, for receiving the data from the photography unit 2110 and the image discrimination unit 2130; an output unit 2150, for receiving the data from the image processing unit 2140; a control unit 2160, for controlling the operation of the image discrimination unit 2130; and a memory 2170 used to store a processing program and various data that are employed by the control unit 160.

The operating sequence for the image processing apparatus 2100 will now be described. The photography unit 2110 receives from a sensor (not shown) X-rays that have passed through a subject (lungs in this embodiment) and obtains an autoradiograph of the front of the lungs. The image information is supplied as digital information to the irradiation area edge portion extraction unit 2120 and the image discrimination unit 2130.

The irradiation area edge portion extraction unit 2120 determines whether diaphragmatic radiation was employed when the image was obtained by the photography unit 2110, and extracts the edge portion of the irradiation area in consonance with the result.

The image discrimination unit 2130 includes a characteristic value calculation unit 2131, an occurrence frequency calculation unit 2132 and a discrimination unit 2133. These components calculate data for a feature (hereinafter also referred to "a characteristic value") for the image obtained by the photography unit 2110, calculates the frequency at which the density value determined by the characteristic value has appeared at the edge portion of the irradiation area that is obtained by the irradiation area edge portion extraction unit 2120, and employs the obtained results to determine the presence/absence of a plain image.

The image processing unit 2140 includes a gradation conversion processing unit 2141, which performs a predetermined conversion process, such as a gradation conversion process, for the image obtained by the photography unit 2110.

The output unit 2150 displays, on a CRT, the image obtained through the predetermined image processing by the image processing unit 2140, and prints the image or outputs it to a film.

Figure 21:
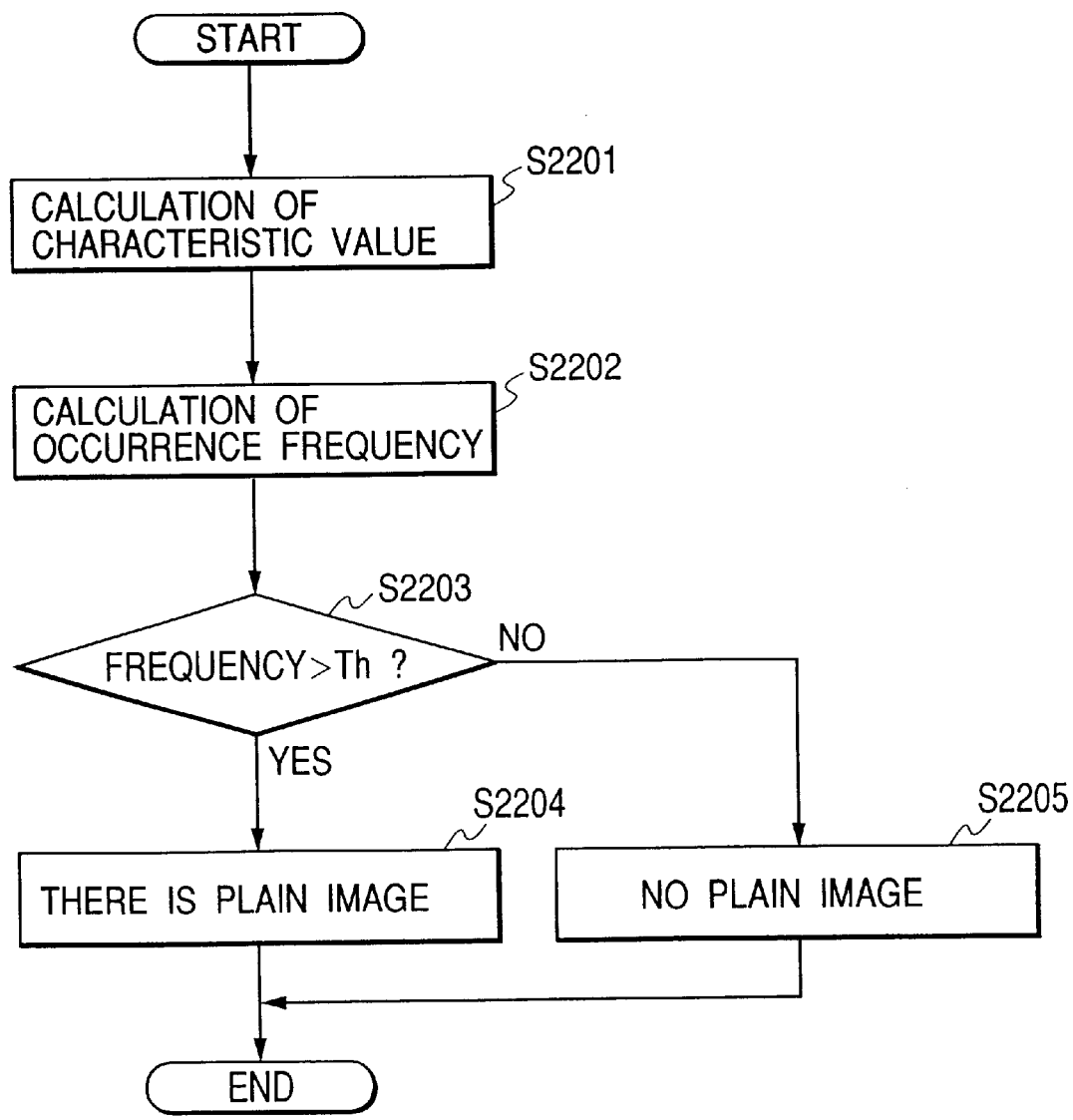
FIG. 21 is a flowchart for explaining the processing performed by the image discrimination apparatus according to the sixth embodiment.

The most important feature of the thus arranged image processing apparatus 2100 is the image discrimination unit 2130. When the processing program in the flowchart in FIG. 21 is read from the memory 2170 and is executed by the control unit 160, the image discrimination unit 2130 is operated as follows.

As the pre-processing performed for the image discrimination unit 2130, the irradiation area edge portion extraction unit 2120 determines whether the image obtained by the photography unit 2110 is an image acquired by the diaphragmatic radiation. This processing will specifically be described.

Figure 1:
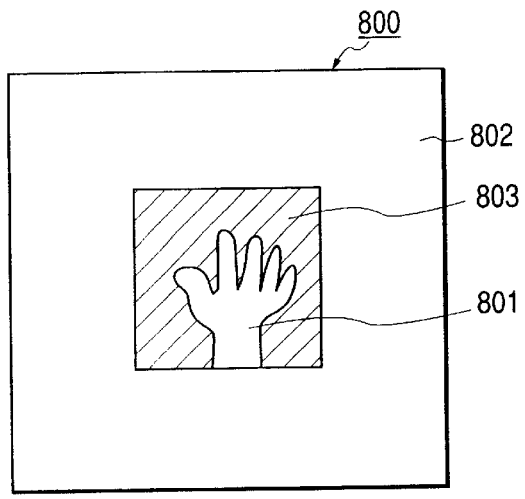
FIG. 1 is a diagram for explaining an autoradiograph obtained by using diaphragmatic radiation.
Figure 2:
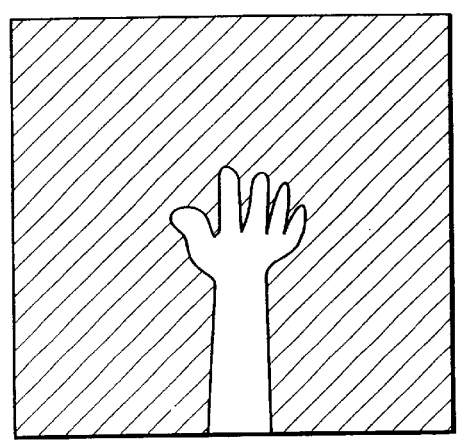
FIG. 2 is a diagram for explaining an autoradiograph obtained without using diaphragmatic radiation.
Figure 3:
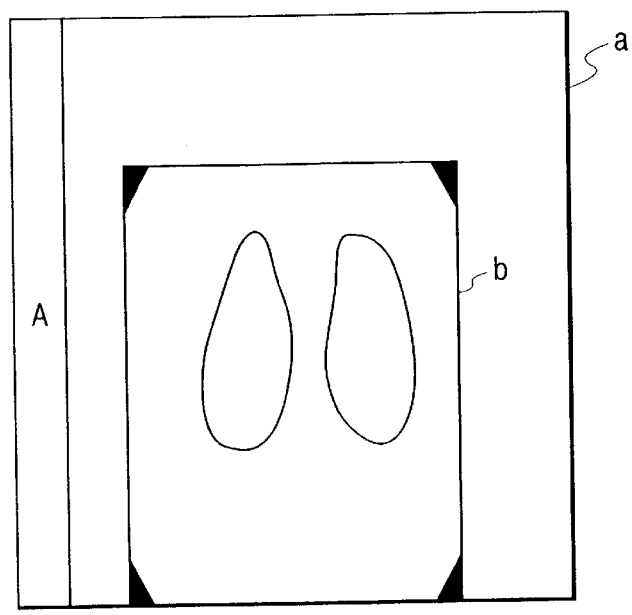
FIG. 3 is a diagram showing an autoradiograph of the chest of a patient obtained by using diaphragmatic radiation.
Figure 4:
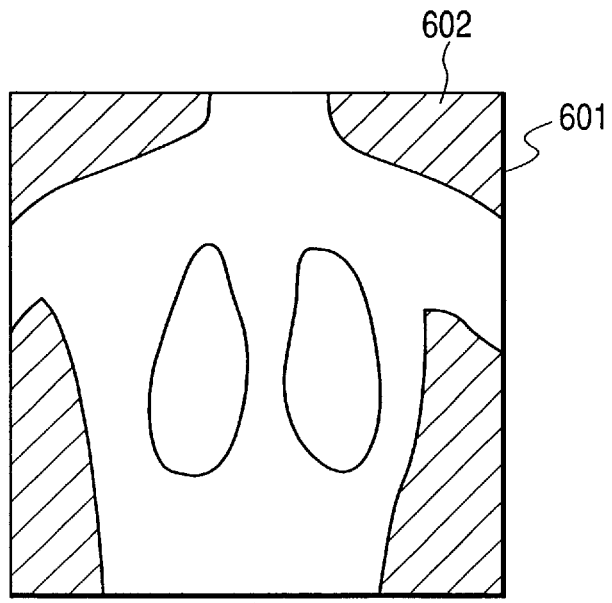
FIG. 4 is a diagram for explaining an autoradiograph of the chest obtained without using diaphragmatic radiation.
Figure 5:
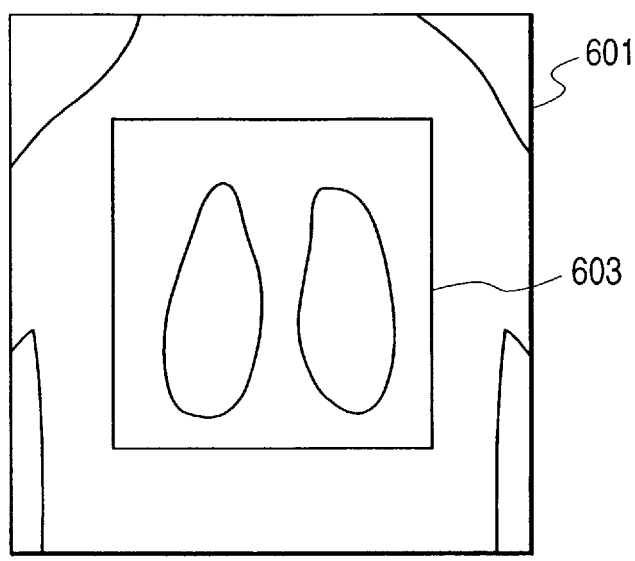
FIG. 5 is a diagram for explaining an autoradiograph of the chest obtained by using diaphragmatic radiation.

The irradiation area edge portion extraction unit 2120 determines whether the image obtained by the photography unit 2110 is an X-ray image obtained without using diaphragmatic radiation, as shown in FIG. 4, or an X-ray image obtained by using diaphragmatic radiation, as shown in FIG. 5. The following determination method is employed, for example.

First, the value MAX for the entire image (the upper portion of the cumulative histogram for the entire image or the upper portion of the sorted density values for the entire image) is obtained as the characteristic value. Then, the frequency is calculated at which a density value having a constant characteristic value ratio has appeared at the edge portion of the image. Following this, a check is performed to determine whether the frequency is equal to or greater than a predetermined threshold value. When the frequency is equal to or greater than the threshold value, it is ascertained that the obtained image is an image obtained without using diaphragmatic radiation. When the frequency is smaller than the threshold value, it is ascertained that the obtained image is an image obtained by using diaphragmatic radiation.

Figure 22:
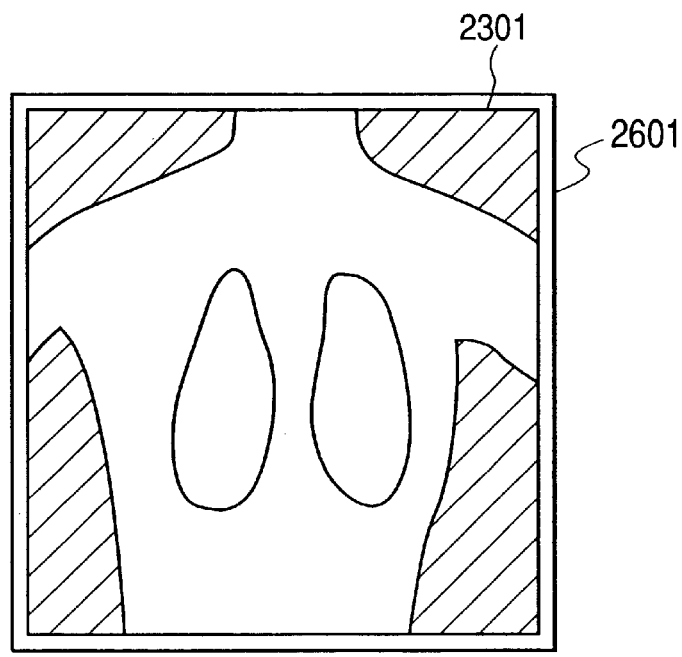
FIG. 22 is a diagram for explaining the edge of the irradiation area in an autoradiograph obtained without using diaphragmatic radiation.
Figure 23:
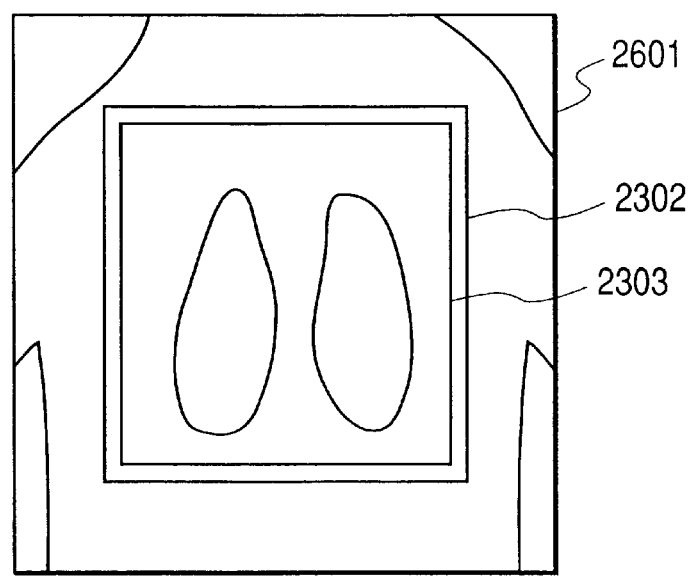
FIG. 23 is a diagram for explaining the edge of the irradiation area in an autoradiograph obtained by using diaphragmatic radiation.

In consonance with the above determination result, the irradiation area edge portion extraction unit 2120 extracts an edge portion 2301 shown in FIG. 22 from an irradiation area for the image obtained without using diaphragmatic radiation (see FIG. 4), and extracts an edge portion 2303 in FIG. 23 for the image obtained by using diaphragmatic radiation.

The irradiation area edge portion 2301 in FIG. 22 corresponds to the edge portion of an irradiation area 601. The edge portion 2303 in FIG. 23 corresponds to the edge portion of a rectangular irradiation area 2302.

Therefore, the information for the image edge portion 2301 or 2302 is extracted in the above described manner by the irradiation area edge portion extraction unit 2120 and is supplied to the image discrimination unit 2130 (specifically, to the occurrence frequency calculation unit 2132).

In the image discrimination unit 2130 (see FIG. 21), first, the characteristic value calculation unit 2131 calculates, as a characteristic value, the value MAX for the image that is obtained by the photography unit 2110 (step S2201).

Assume that the value MAX is the upper point (5% point, etc.) in the cumulative histogram for the entire image.

The value MAX is not limited to the upper point in the cumulative histogram, but may be the upper point among the density values that are sorted for the image.

The occurrence frequency calculation unit 2132 calculates the frequency at which the density value having a constant ratio (e.g., 90% or higher) for the characteristic value (value MAX), which is obtained by the characteristic value calculation unit 2131, has appeared at the irradiation edge portion 2301 or 2303 (see FIG. 22 or 23) that is extracted by the irradiation area edge portion extraction unit 2120 (step S2202).

The discrimination unit 2133 determines whether the frequency obtained by the frequency calculation unit 2132 is greater than a predetermined threshold value Th (step S2203).

When, as a result of the determination, the frequency >Th, the discrimination unit 2133 ascertains that the image obtained by the photography unit 2110 includes a plain image (step S2204). When the frequency >Th is not established, the discrimination unit 2133 ascertains that the image obtained by the photography unit 2110 does not include a plain image (step S2205).

As is described above, in this embodiment, the presence/absence of a plain image portion in an obtained image is ascertained by using the frequency at which the density value for the image, which is determined using the value MAX (characteristic value), has appeared at the edge portion 2301 or 2303 in the irradiation area. That is, based on the facts that the plain image always appears in the edge portion of the irradiation area and that the density value in the plain image is high in the irradiation area, when the frequency at which the density value has appeared in the irradiation area is greater than a predetermined value (Th), it is ascertained that a plain image exists. When the frequency is not greater than the predetermined value, it is ascertained that no plain image exists.

With this arrangement, even when an image to be identified is an image obtained by using diaphragmatic radiation, as shown in FIG. 5 or 23, the lungs in the irradiation area will not be mistakenly determined to be a plain image. Therefore, the presence/absence of the plain image can be precisely determined. Further, since such a determination is performed by using the frequency at which the density value, which is determined from the value MAX (characteristic value) in the autoradiograph, has appeared at the edge portion of the irradiation area, a consistent determination can be provided. In addition, since the image processing unit 2140 can perform such image processing as a gradation conversion process, in consonance with the accurately and consistently provided determination result as to the presence/absence of a plain image, the image processing unit 2140 can transmit a preferable resultant image to the output unit 2150. In addition, since the image processing performed by the image processing unit 2140 can be changed in consonance with the result obtained when the determination of the presence/absence of a plain image is made, appropriate image processing can be performed.

The characteristic value (value MAX), which is employed by the irradiation area edge portion extraction unit 2120 to determine whether the diaphragmatic radiation was performed, may be calculated by the characteristic value calculation unit 2131 in the image discrimination unit 2130. In other words, the characteristic value calculation unit 2131 may be used in common by the irradiation area edge portion extraction unit 2120 and the image discrimination unit 2130.

In a seventh embodiment, a characteristic value calculation unit 2131 in FIG. 20 calculates a characteristic value by using a density value histogram for an autoradiograph.

Figure 24:
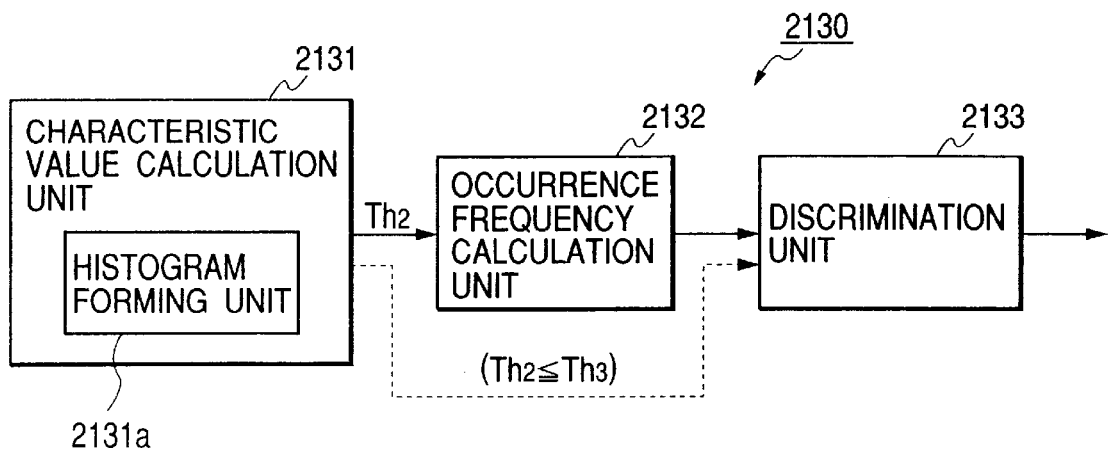
FIG. 24 is a diagram illustrating the arrangement of an image discrimination unit in an image discrimination apparatus according to a seventh embodiment of the present invention.
Figure 25:
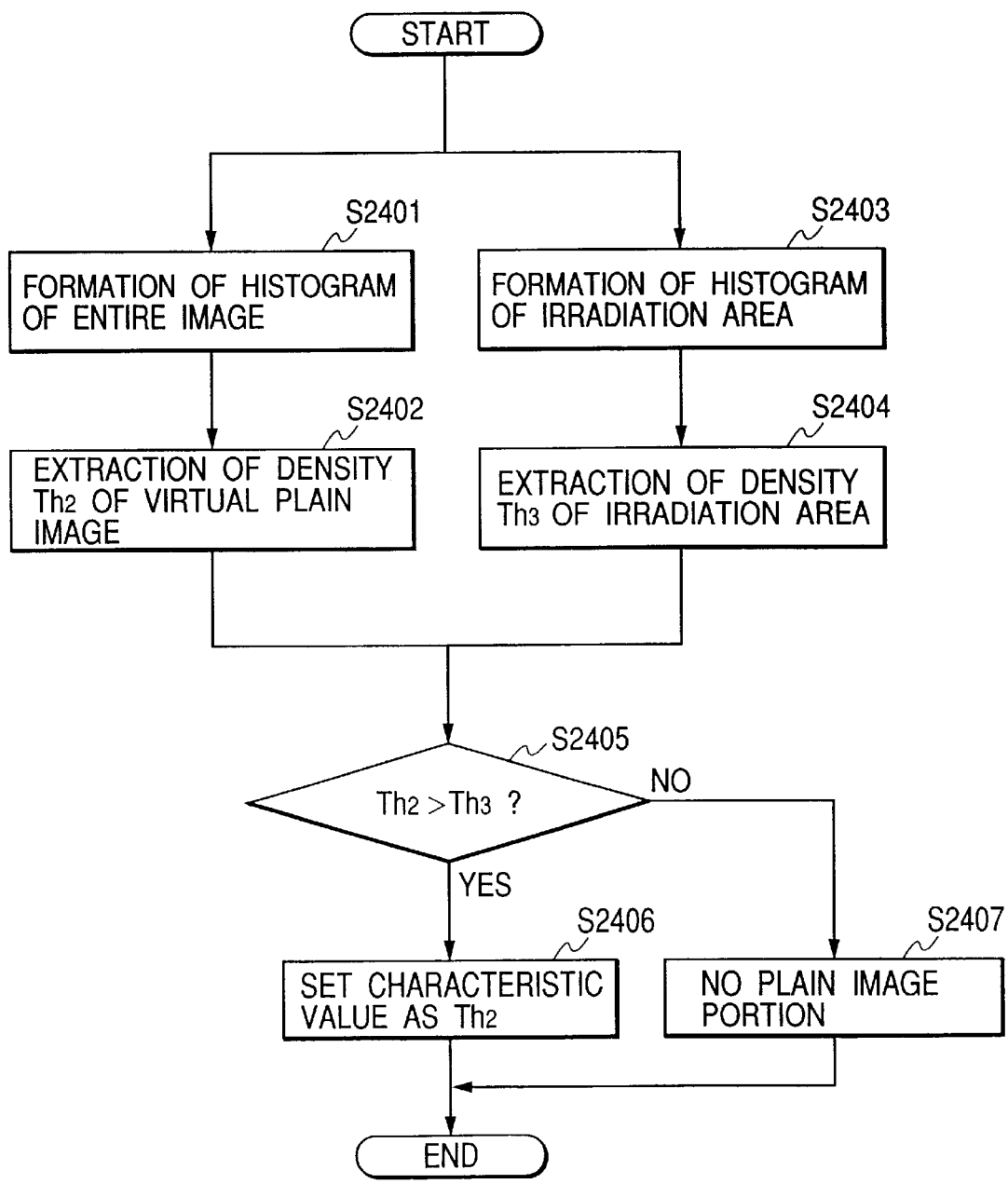
FIG. 25 is a flowchart for explaining the processing performed by a characteristic value calculation unit in the image discrimination apparatus according to the seventh embodiment.

As is shown in FIG. 24, the characteristic value calculation unit 2131 includes a histogram forming unit 2131a, and is operated as follows when the processing program shown in the flowchart in FIG. 25 is read from a memory 2170 and is executed by a control unit 2160.

Figure 26:
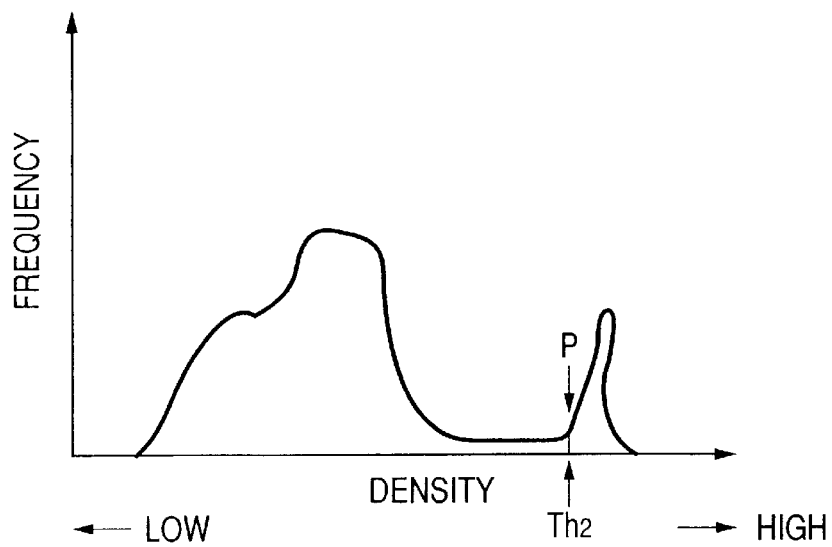
FIG. 26 is a graph for explaining a density value histogram, for a complete autoradiograph, that is provided by the characteristic value calculation unit.

First, the histogram forming unit 2131a forms a density value histogram, shown in FIG. 26, wherein the horizontal axis represents a density value and the vertical axis represents a frequency (step S2401).

A density value $Th_2$ that indicates the lower limit of the density in a virtual plain image is extracted from the density value histogram formed at step S2401 (step S2402). It is assumed in this embodiment that in the density value histogram the density value $Th_2$ is the density value at the deepest point P in the first dent portion on the maximum density side.

An irradiation area is extracted from the autoradiograph by using the above described method for determining the performance of diaphragmatic radiation, and a density value histogram for the irradiation area is formed (step S2403).

The density value $Th_3$ at an upper x% (e.g., the upper 40%) is extracted from the density value histogram formed at step S2403 (step S2404).

When the density values $Th_2$ and $Th_3$ are extracted at steps S2402 and S2403, these values are compared (step S2405).

If $Th_2 > Th_3$, it is assumed that a virtual plain image is present, and the characteristic value $Th_2$ is output (step S2406).

When $Th_2 \leq Th_3$, it is assumed that there is no plain image, and information to that effect is output (step S2407). This is because, as is described above, the density value in the plain image is high in the irradiation area and it can be ascertained that there is no plain image if the density value $Th_2$ (lower density limit) in the virtual plain image is smaller than the density value $Th_3$ (the high density value) in the irradiation area.

As is described above, the characteristic value $Th_2$, or such information as that there is "no plain image," that is output by the characteristic value calculation unit 2131 is transmitted to the occurrence frequency calculation unit 2132 or to the discrimination unit 2133.

Specifically, as is shown in FIG. 24, when the characteristic value $Th_2$ is output by the characteristic value calculation unit 2131 (when a virtual plain image is present), the characteristic value $Th_2$ is transmitted to the occurrence frequency calculation unit 2132 and is employed as the above described characteristic value Th (value MAX) (see solid line in FIG. 24). Hereinafter, the determination of the actual plain image is performed in the above described manner.

When such the information as that there is "no plain image" is output by the characteristic value calculation unit 2131, the information is transmitted unchanged through the discrimination unit 2133 to the image processing unit 2140 (see broken line in FIG. 24).

As is described above, in this embodiment, the density value (lower density limit) $Th_2$ in the virtual plain image is obtained from the shape of the density value histogram for the autoradiograph, and is compared with the density value (high density value) $Th_3$, which is obtained from the shape of the density value histogram for the irradiation area, so that the presence/absence of a virtual plain image can be determined. When a virtual plain image is present, the density value $Th_2$ in the virtual plain image is employed as the characteristic value in order to detect the presence/absence of an actual plain image.

With this arrangement, the absence of a plain image can be precisely determined. Further, when the presence of a virtual plain image is determined, the constant characteristic value (density value $Th_2$) can be employed to detect the presence/absence of the actual plain image, so that a more accurate determination of the presence/absence of a plain image can be made.

The objectives of the present invention are achieved as follows: a memory medium on which is stored software program code for implementing the functions of a host computer or a terminal in the above described embodiments is supplied to a system or to an apparatus, and the computer (or a CPU or an MPU) in the system or the apparatus reads the program code from the memory medium.

In this case, the program code read from the memory medium accomplishes the functions of the above described embodiments, and the memory medium on which such program code is recorded constitutes the present invention.

A memory medium for supplying such program code can be, for example, a ROM, a floppy disk, a hard disk, an optical disk, a magneto optical disk, a CD-ROM, a CD-R, a magnetic tape or a nonvolatile memory card.

In addition, the scope of the present invention includes not only a case where the functions in the above described embodiments can be performed when program code is read and executed by the computer, but also a case where, according to an instruction in the program code, an OS running on the computer, etc., performs one part, or all, of the actual processing to accomplish the functions included in the above embodiments.

Furthermore, in order to implement the functions included in the above described embodiments, the present invention includes a case where program code, read from a memory medium, is written in a memory that is mounted on a function expansion board inserted into a computer, or a function expansion unit connected to a computer, and in consonance with a program code instruction, a CPU mounted on the function expansion board, or on the function expansion unit, performs one part, or all, of the actual processing.

Many widely different embodiments of the present invention may be constructed without departing from the spirit and scope of the present invention. It should be understood that the present invention is not limited to the specific embodiments described in the specification, except as defined in the appended claims.

What is claimed is:

1. An image discriminating apparatus, which determines whether a designated portion of a radiograph of an object includes an irradiation area, comprising:
   (A) first characteristic value calculation means for calculating a first characteristic value as a representing value of a pixel value representing an irradiation area from an input radiographic image signal;
   (B) second characteristic value calculation means for dividing the image into a plurality of small regions and calculating second characteristic values representing a pixel in each of the small regions;
   (C) discrimination means, in a case that the second characteristic value is larger than the first characteristic value, for determining that the small region in which a second characteristic value is calculated includes an irradiation area, and discriminating a whole irradiation area from the small region in which the irradiation area is included.

2. An image discrimination apparatus according to claim 1, wherein said first characteristic value calculation means assigns a value relating to a maximum density value, an average density value, or a middle density value of pixels in an image as a representing value representing an irradiation area.

3. An image discrimination apparatus according to claim 1, wherein said second characteristic value calculation means is so arranged as to be able to obtain as said second characteristic value any one of a maximum density value, an average density value, and a middle density value of pixels which constitute each of said plurality of designated portions of said radiograph.

4. An image discrimination apparatus according to claim 1, wherein said first characteristic value calculation means is so arranged as to be able to form a histogram for density values of pixels which constitute said radiograph, and to calculate said first characteristic value based on said histogram.

5. An image discrimination apparatus according to claim 4, wherein said first characteristic value is a density value at the deepest point in a dent portion which first occurs on the maximum density value side in said histogram.

6. An image discrimination apparatus according to claim 1, further comprising a memory medium which is readable by a computer in which is stored a program for permitting said first characteristic value calculation means, said second characteristic value calculation means and said discrimination means to perform processing, and which is so arranged that the processing of said image discrimination apparatus is controlled by said computer which is operated by said program stored in said memory medium.

7. An image discriminating apparatus, which determines whether a designated portion of a radiograph of an object includes an irradiation area, comprising:
   (A) first characteristic value calculation means for calculating a first characteristic value as a representing value representing an irradiation area from an input radiographic image signal;
   (B) radiograph occurrence frequency calculation means for dividing the image into a plurality of small regions and calculating a value as an occurrence frequency representing a number of pixels having a value more than the first characteristic value in each of the small regions; and
   (C) discrimination means, in a case where the occurrence frequency is more than a predetermined value, for determining that the small region to calculate the occurrence frequency includes an irradiation area.

8. An image discrimination apparatus according to claim 7, wherein said first characteristic value calculation means is so arranged as to obtain, as said first characteristic value, a maximum density value for a pixel which constitutes said radiograph.

9. An image discrimination apparatus according to claim 7, wherein said first characteristic value calculation means is so arranged as to be able to form a histogram for density values of pixels which constitute said radiograph, and to calculate said first characteristic value based on said histogram.

10. An image discrimination apparatus according to claim 9, wherein said first characteristic value is a density value at the deepest point in a dent portion which first occurs on the maximum density value side in said histogram.

11. An image discrimination apparatus according to claim 7, further comprising a memory medium which is readable by a computer in which is stored a program for permitting said first characteristic value calculation means, said second characteristic value calculation means and said discrimination means to perform processing, and which is so arranged that a processing of said image discrimination apparatus is controlled by said computer which is operated by said program stored in said memory medium.

12. An image discrimination apparatus according to claim 7, wherein the discrimination means discriminates a whole irradiation area from the small regions wherein it is determined that the irradiation area is included.

13. An image discrimination method, of determining whether a designated portion of a radiograph of an object includes an irradiation area, comprising:
   (A) first characteristic value calculation step of calculating a first characteristic value as a representing value of a pixel value representing an irradiation area from an input radiographic image signal;
   (B) second characteristic value calculation step of dividing the image into a plurality of small regions and calculating a second characteristic value representing a pixel in each of the small regions; and
   (C) discrimination step, in a case where the second characteristic value is more than the first characteristic value, of determining that a small region in which a second characteristic value is calculated includes an irradiation area, and discriminating a whole irradiation area from the small region wherein it is determined that the irradiation area is included.

14. An image discrimination method, for determining whether a designated portion of a radiograph includes an irradiation area, comprising:
   (A) a first characteristic value calculation step of calculating a first characteristic value as a representing value representing an irradiation area from an input radiographic image signal;
   (B) radiographic occurrence frequency calculation step of dividing the image into a plurality of small regions and calculating a value as an occurrence frequency representing a number of pixels having a value more than the first characteristic value in each of the small regions; and (C) discrimination step, in a case where the occurrence frequency is more than a predetermined value, for determining that the small region to calculate the occurrence frequency includes an irradiation area.

15. An image discrimination apparatus, which detects presence/absence of a direct irradiation area in a radiograph, wherein said direct irradiation area is an area where radiation does not pass through an object but is directly incident onto a sensor, comprising:

(A) characteristic value calculation means for calculating a first characteristic value as a representing value representing an irradiation area from an input radiographic image signal;

(B) radiograph occurrence frequency calculation means for calculating an occurrence frequency representing a number of pixels having a value more than the first characteristic value in a predetermined region; and (C) determination means, in a case where the occurrence frequency is equal to or more than a predetermined value, for determining that the predetermined region having said direct irradiation area includes said direct irradiation area.

16. An image discrimination method, for detecting the presence/absence of a direct irradiation area in a radiograph, wherein said direct irradiation area is in an area where radiation does not pass through an object but is directly incident onto a sensor, comprising:

(A) a characteristic value calculation step of calculating a first characteristic value as a representing value representing an irradiation area from an input radiographic image signal;

(B) a radiograph occurrence frequency calculation step of calculating an occurrence frequency representing a number of pixels having a value more than the first characteristic value in a predetermined region; and (C) a discrimination step, in a case where the occurrence frequency is equal to or more than a predetermined value, of determining that the predetermined region having said direct irradiation area includes said direct irradiation area.

* * * * *